(12) United States Patent
Perata et al.

(10) Patent No.: US 11,891,611 B2
(45) Date of Patent: Feb. 6, 2024

(54) METHOD FOR MODULATING PLANT PROCESSES

(71) Applicant: VALAGRO S.P.A., Atessa (IT)

(72) Inventors: Pierdomenico Perata, San Giuliano Terme (IT); Elena Loreti, Pisa (IT); Eleonora Paparelli, San Giuliano Terme (IT); Antonietta Santaniello, Pisa (IT); Giacomo Novi, Buti (IT); Alberto Piaggesi, Lanciano (IT)

(73) Assignee: VALAGRO S.P.A, Atessa (IT)

( * ) Notice: Subject to any disclaimer, the term of this patent is extended or adjusted under 35 U.S.C. 154(b) by 0 days.

(21) Appl. No.: 15/502,135

(22) PCT Filed: Aug. 6, 2015

(86) PCT No.: PCT/IB2015/055974
§ 371 (c)(1),
(2) Date: Feb. 6, 2017

(87) PCT Pub. No.: WO2016/020874
PCT Pub. Date: Feb. 11, 2016

(65) Prior Publication Data
US 2017/0226509 A1    Aug. 10, 2017

Related U.S. Application Data

(60) Provisional application No. 62/033,757, filed on Aug. 6, 2014.

(30) Foreign Application Priority Data

Aug. 6, 2014    (IT) .......................... MI2014A001447

(51) Int. Cl.
| | | |
|---|---|---|
| C12N 15/82 | (2006.01) | |
| C12N 15/113 | (2010.01) | |
| A01N 65/03 | (2009.01) | |
| C05B 7/00 | (2006.01) | |
| C05C 5/02 | (2006.01) | |
| C05C 5/04 | (2006.01) | |
| C05D 1/02 | (2006.01) | |
| C05D 5/00 | (2006.01) | |
| C05D 9/02 | (2006.01) | |

(52) U.S. Cl.
CPC ......... *C12N 15/8262* (2013.01); *A01N 65/03* (2013.01); *C05B 7/00* (2013.01); *C05C 5/02* (2013.01); *C05C 5/04* (2013.01); *C05D 1/02* (2013.01); *C05D 5/00* (2013.01); *C05D 9/02* (2013.01); *C12N 15/113* (2013.01); *C12N 2310/141* (2013.01); *C12N 2330/10* (2013.01)

(58) Field of Classification Search
None
See application file for complete search history.

(56) References Cited

U.S. PATENT DOCUMENTS

| | | | | |
|---|---|---|---|---|
| 5,973,137 A | * | 10/1999 | Heath | ................. C12N 15/1003 435/91.3 |
| 2011/0296556 A1 | * | 12/2011 | Sammons | ........... C12N 15/8206 435/410 |
| 2012/0272408 A1 | * | 10/2012 | Maor | .................... C12N 15/113 800/278 |
| 2014/0215656 A1 | | 7/2014 | Crawford et al. | |

FOREIGN PATENT DOCUMENTS

| | | |
|---|---|---|
| CN | 102899352 | 1/2013 |
| EP | 2468902 | 6/2012 |
| WO | 2013016201 | 1/2013 |
| WO | 2014113423 | 7/2014 |

OTHER PUBLICATIONS

Kim et al. (Plant Cell Rep (2009) 28:1159-1167).*
Shekoofa et al. Journal of agronomy 7.1 (2008): 41.*
Gan et al. Plant Cell Rep (2010) 29:1261-1268.*
Claros et al. Biochemical Education 27 (1999) 110-113.*
Conn et al. Plant methods 9.1 (2013): 4.*
Conn et al. Plant methods 9.1 (2013): 4, Supplement.*
Jones-Rhoades et al. (Molecular Cell, vol. 14, 787-799, Jun. 18, 2004).*
Branscheid et al. (MPMI vol. 23, No. 7, 2010, pp. 915-926).*
Blunden, et al. Journal of applied phycology 8.6 (1996): 535-543. (Year: 1996).*
Conn et al. (Plant methods 9.1 (2013): 4). (Year: 2013).*
Conn et al. (Plant methods & nbsp;9.1 (2013): 4). (Year: 2013).*
Gan et al. (Plant Cell Rep (2010) 29:1261-1268). (Year: 2010).*
Claros et al. (Biochemical Education 27 (1999) 110-113). (Year: 1999).*
Shekoofa et al. (Journal of agronomy 7.1 (2008): 41). (Year: 2008).*
Sunkar, (Seminars in cell & developmental biology. vol. 21. No. 8. Academic Press, 2010). (Year: 2010).*
Marín-González et al. (Plant science 196 (2012): 18-30). (Year: 2012).*
Bano, et al. (Functional plant biology 29.11 (2002): 1299-1307). (Year: 2002).*
Zabala et al. (BMC plant biology 12.1 (2012): 1-26). (Year: 2012).*
Yu et al. (Biochemical systematics and ecology 31.2 (2003): 129-139). (Year: 2003).*
Aubert et al. "RD20, a stress-inducible caleosin, participates in stomatal control, transpiration and drought tolerance in *Arabidopsis thaliana*." Plant and Cell Physiology 51.12 (2010): 1975-1987. (Year: 2010).*
International Search Report and Written Opinion issued in International Application No. PCT/IB2015/055974 dated Nov. 26, 2015.

(Continued)

*Primary Examiner* — Charles Logsdon
(74) *Attorney, Agent, or Firm* — BakerHostetler

(57) ABSTRACT

The present invention relates to a method for modulating plant processes said method being characterized in that a plant is fed with an eco-friendly, plant- and/or algae-derived, biostimulant composition comprising exogenous small RNA molecules. In particular, the method of the invention can be used for modulating physiological or pathological plant processes, such plant growth, plant productivity, fruit quality, quality of produce, plant yield, plant response to abiotic stress and plant resistance to diseases or to infections.

13 Claims, 11 Drawing Sheets

Specification includes a Sequence Listing.

(56) References Cited

OTHER PUBLICATIONS

Marina et al., "Post-transcriptional gene silencing and virus resistance in Nicotiana benthamiana expressing a Grapevine virus A minireplicon", Transgenic Research, vol. 18, No. 3, 2008, pp. 331-345.
Nan Gao et al., "Transgenic tomato overexpressing ath-miR399d has enhanced phosphorus accumulation through increased acid phosphatase and proton secretion as well as phosphate transporters", Plant and Soil; An International Journal on Plant-Soil Relationships, Kluwer Academic Publishers, Do., vol. 334, No. 1-2, 2009, pp. 123-136.
Rodriguez-Medina Caren, et al., "Macromolecular composition of phloem exudate from white lupin (*Lupinus albus* L.)", Bmc Plant Biology, Biomed Central, London, GB, vol. 11, No. 1, 2011, p. 36.
H. Restrepo-Diaz et al., "Leaf Potassium Accumulation in Olive Plants Related to Nutritional K Status, Leaf Age, and Foliar Application of Potassium Salts", Journal of Plant Nutrition, vol. 32, No. 7, 2009, pp. 1108-1121.
R. Xia, et al., "MicroRNA Superfamilies Descended from miR390 and Their Roles in Secondary Small Interfering RNA Biogenesis in Eudicots", The Plant Cell, vol. 25, No. 5, 2013, pp. 1555-1572.
Search Report issued in Italian Application No. ITMI20141447 dated Mar. 25, 2015.
Brosnan, et al., miRNA communication on another level, Nature Plants, Oct. 2021, vol. 7, pp. 1328-1329.

\* cited by examiner

SEQUENCE LISTING

```
<160> NUMBER OF SEQ ID NOS: 44

<210> SEQ ID NO 1
<211> LENGTH: 21
<212> TYPE: DNA
<213> ORGANISM: Artificial Sequence
<220> FEATURE:
<223> OTHER INFORMATION: miR-166

<400> SEQUENCE: 1
agaatgtcgt ctggttcgag a                                        21

<210> SEQ ID NO 2
<211> LENGTH: 21
<212> TYPE: DNA
<213> ORGANISM: Artificial Sequence
<220> FEATURE:
<223> OTHER INFORMATION: miR-166

<400> SEQUENCE: 2
gggatgttgt ctggctcgac a                                        21

<210> SEQ ID NO 3
<211> LENGTH: 21
<212> TYPE: DNA
<213> ORGANISM: Artificial Sequence
<220> FEATURE:
<223> OTHER INFORMATION: miR-166

<400> SEQUENCE: 3
tcggaccagg cttcaatccc t                                        21

<210> SEQ ID NO 4
<211> LENGTH: 18
<212> TYPE: DNA
<213> ORGANISM: Artificial Sequence
<220> FEATURE:
<223> OTHER INFORMATION: miR-166

<400> SEQUENCE: 4
tcggaccagg cttcattc                                            18

<210> SEQ ID NO 5
<211> LENGTH: 19
<212> TYPE: DNA
<213> ORGANISM: Artificial Sequence
<220> FEATURE:
<223> OTHER INFORMATION: miR-166
```

```
<400> SEQUENCE: 5
tcggaccagg cttcattcc                                                    19

<210> SEQ ID NO 6
<211> LENGTH: 21
<212> TYPE: DNA
<213> ORGANISM: Artificial Sequence
<220> FEATURE:
<223> OTHER INFORMATION: miR-166

<400> SEQUENCE: 6
tcggaccagg cttcattccc c                                                 21

<210> SEQ ID NO 7
<211> LENGTH: 21
<212> TYPE: DNA
<213> ORGANISM: Artificial Sequence
<220> FEATURE:
<223> OTHER INFORMATION: miR-166

<400> SEQUENCE: 7
tcggaccagg cttcattccc t                                                 21

<210> SEQ ID NO 8
<211> LENGTH: 21
<212> TYPE: DNA
<213> ORGANISM: Artificial Sequence
<220> FEATURE:
<223> OTHER INFORMATION: miR-166

<400> SEQUENCE: 8
tcggaccagg cttcattcct c                                                 21

<210> SEQ ID NO 9
<211> LENGTH: 21
<212> TYPE: DNA
<213> ORGANISM: Artificial Sequence
<220> FEATURE:
<223> OTHER INFORMATION: miR-166

<400> SEQUENCE: 9
tctcggacca ggcttcattc c                                                 21

<210> SEQ ID NO 10
<211> LENGTH: 21
<212> TYPE: DNA
<213> ORGANISM: Artificial Sequence
<220> FEATURE:
<223> OTHER INFORMATION: miR-166

<400> SEQUENCE: 10
ttggaccagg cttcattccc c                                                 21

<210> SEQ ID NO 11
<211> LENGTH: 21
<212> TYPE: DNA
<213> ORGANISM: Artificial Sequence
<220> FEATURE:
<223> OTHER INFORMATION: miR-398

<400> SEQUENCE: 11
gggttgattt gagaacatat g                                                 21

<210> SEQ ID NO 12
<211> LENGTH: 21
```

```
<212> TYPE: DNA
<213> ORGANISM: Artificial Sequence
<220> FEATURE:
<223> OTHER INFORMATION: miR-398

<400> SEQUENCE: 12
tatgttctca ggtcgcccct g                                          21

<210> SEQ ID NO 13
<211> LENGTH: 21
<212> TYPE: DNA
<213> ORGANISM: Artificial Sequence
<220> FEATURE:
<223> OTHER INFORMATION: miR-168

<400> SEQUENCE: 13
cccgccttgc atcaactgaa t                                          21

<210> SEQ ID NO 14
<211> LENGTH: 21
<212> TYPE: DNA
<213> ORGANISM: Artificial Sequence
<220> FEATURE:
<223> OTHER INFORMATION: miR-168

<400> SEQUENCE: 14
cctgccttgc atcaactgaa t                                          21

<210> SEQ ID NO 15
<211> LENGTH: 22
<212> TYPE: DNA
<213> ORGANISM: Artificial Sequence
<220> FEATURE:
<223> OTHER INFORMATION: miR-168

<400> SEQUENCE: 15
tcccgccttg caccaagtga at                                         22

<210> SEQ ID NO 16
<211> LENGTH: 21
<212> TYPE: DNA
<213> ORGANISM: Artificial Sequence
<220> FEATURE:
<223> OTHER INFORMATION: miR-168

<400> SEQUENCE: 16
tcgcttggtg cagatcggga c                                          21

<210> SEQ ID NO 17
<211> LENGTH: 21
<212> TYPE: DNA
<213> ORGANISM: Artificial Sequence
<220> FEATURE:
<223> OTHER INFORMATION: miR-168

<400> SEQUENCE: 17
tcgcttggtg caggtcggga c                                          21

<210> SEQ ID NO 18
<211> LENGTH: 21
<212> TYPE: DNA
<213> ORGANISM: Artificial Sequence
<220> FEATURE:
<223> OTHER INFORMATION: miR-396

<400> SEQUENCE: 18
```
gttcaataaa gctgtgggaa g                                              21

<210> SEQ ID NO 19
<211> LENGTH: 21
<212> TYPE: DNA
<213> ORGANISM: Artificial Sequence
<220> FEATURE:
<223> OTHER INFORMATION: miR-396

<400> SEQUENCE: 19
ttccacagct ttcttgaact t                                              21

<210> SEQ ID NO 20
<211> LENGTH: 21
<212> TYPE: DNA
<213> ORGANISM: Artificial Sequence
<220> FEATURE:
<223> OTHER INFORMATION: miR-159

<400> SEQUENCE: 20
tttggattga agggagctct a                                              21

<210> SEQ ID NO 21
<211> LENGTH: 22
<212> TYPE: DNA
<213> ORGANISM: Artificial Sequence
<220> FEATURE:
<223> OTHER INFORMATION: miR-6027

<400> SEQUENCE: 21
atgggtagca caaggattaa tg                                             22

<210> SEQ ID NO 22
<211> LENGTH: 22
<212> TYPE: DNA
<213> ORGANISM: Artificial Sequence
<220> FEATURE:
<223> OTHER INFORMATION: miR-6027

<400> SEQUENCE: 22
tgaatccttc ggctatccat aa                                             22

<210> SEQ ID NO 23
<211> LENGTH: 21
<212> TYPE: DNA
<213> ORGANISM: Artificial Sequence
<220> FEATURE:
<223> OTHER INFORMATION: miR-6024

<400> SEQUENCE: 23
tttagcaaga gttgttttac c                                              21

<210> SEQ ID NO 24
<211> LENGTH: 22
<212> TYPE: DNA
<213> ORGANISM: Artificial Sequence
<220> FEATURE:
<223> OTHER INFORMATION: miR-6024

<400> SEQUENCE: 24
ttttagcaag agttgtttta cc                                             22

<210> SEQ ID NO 25
<211> LENGTH: 21
<212> TYPE: DNA
<213> ORGANISM: Artificial Sequence

```
<220> FEATURE:
<223> OTHER INFORMATION: miR-162

<400> SEQUENCE: 25
tcgataaacc tctgcatcca g                                              21

<210> SEQ ID NO 26
<211> LENGTH: 21
<212> TYPE: DNA
<213> ORGANISM: Artificial Sequence
<220> FEATURE:
<223> OTHER INFORMATION: miR-156

<400> SEQUENCE: 26
gcttactctc tatctgtcac c                                              21

<210> SEQ ID NO 27
<211> LENGTH: 21
<212> TYPE: DNA
<213> ORGANISM: Artificial Sequence
<220> FEATURE:
<223> OTHER INFORMATION: miR-156

<400> SEQUENCE: 27
ttgacagaag atagagagca c                                              21

<210> SEQ ID NO 28
<211> LENGTH: 21
<212> TYPE: DNA
<213> ORGANISM: Artificial Sequence
<220> FEATURE:
<223> OTHER INFORMATION: miR-157

<400> SEQUENCE: 28
ttgacagaag atagagagca c                                              21

<210> SEQ ID NO 29
<211> LENGTH: 21
<212> TYPE: DNA
<213> ORGANISM: Artificial Sequence
<220> FEATURE:
<223> OTHER INFORMATION: miR-9471

<400> SEQUENCE: 29
ttggctgagt gagcatcacg g                                              21

<210> SEQ ID NO 30
<211> LENGTH: 20
<212> TYPE: DNA
<213> ORGANISM: Artificial Sequence
<220> FEATURE:
<223> OTHER INFORMATION: miR-9471

<400> SEQUENCE: 30
ttggctgagt gagcatcact                                                20

<210> SEQ ID NO 31
<211> LENGTH: 21
<212> TYPE: DNA
<213> ORGANISM: Artificial Sequence
<220> FEATURE:
<223> OTHER INFORMATION: miR-9471

<400> SEQUENCE: 31
ttggctgagt gagcatcact g                                              21
```

<210> SEQ ID NO 32
<211> LENGTH: 21
<212> TYPE: DNA
<213> ORGANISM: Artificial Sequence
<220> FEATURE:
<223> OTHER INFORMATION: miR-390

<400> SEQUENCE: 32
aagctcagga gggatagcac c                                              21

<210> SEQ ID NO 33
<211> LENGTH: 21
<212> TYPE: DNA
<213> ORGANISM: Artificial Sequence
<220> FEATURE:
<223> OTHER INFORMATION: miR-390

<400> SEQUENCE: 33
aagctcagga gggatagcgc c                                              21

<210> SEQ ID NO 34
<211> LENGTH: 20
<212> TYPE: DNA
<213> ORGANISM: Artificial Sequence
<220> FEATURE:
<223> OTHER INFORMATION: miR-169

<400> SEQUENCE: 34
tagccaagga tgacttgcct                                                20

<210> SEQ ID NO 35
<211> LENGTH: 21
<212> TYPE: DNA
<213> ORGANISM: Artificial Sequence
<220> FEATURE:
<223> OTHER INFORMATION: miR-1919

<400> SEQUENCE: 35
tgtcgcagat gactttcgcc c                                              21

<210> SEQ ID NO 36
<211> LENGTH: 21
<212> TYPE: DNA
<213> ORGANISM: Artificial Sequence
<220> FEATURE:
<223> OTHER INFORMATION: miR-397

<400> SEQUENCE: 36
attgagtgca gcgttgatga c                                              21

<210> SEQ ID NO 37
<211> LENGTH: 21
<212> TYPE: DNA
<213> ORGANISM: Artificial Sequence
<220> FEATURE:
<223> OTHER INFORMATION: miR-414

<400> SEQUENCE: 37
tcatcctcat catcatcgtc c                                              21

<210> SEQ ID NO 38
<211> LENGTH: 21
<212> TYPE: DNA
<213> ORGANISM: Artificial Sequence
<220> FEATURE:
<223> OTHER INFORMATION: miR-4376

```
<400> SEQUENCE: 38
tacgcaggag agatgatgct g                                              21

<210> SEQ ID NO 39
<211> LENGTH: 22
<212> TYPE: DNA
<213> ORGANISM: Artificial Sequence
<220> FEATURE:
<223> OTHER INFORMATION: miR-482

<400> SEQUENCE: 39
tcttgcctac accgcccatg cc                                             22

<210> SEQ ID NO 40
<211> LENGTH: 21
<212> TYPE: DNA
<213> ORGANISM: Artificial Sequence
<220> FEATURE:
<223> OTHER INFORMATION: miR-5168

<400> SEQUENCE: 40
tcggaccagg cttcaatccc t                                              21

<210> SEQ ID NO 41
<211> LENGTH: 22
<212> TYPE: DNA
<213> ORGANISM: Artificial Sequence
<220> FEATURE:
<223> OTHER INFORMATION: miR-5300

<400> SEQUENCE: 41
tccccagtcc aggcattcca ac                                             22

<210> SEQ ID NO 42
<211> LENGTH: 21
<212> TYPE: DNA
<213> ORGANISM: Artificial Sequence
<220> FEATURE:
<223> OTHER INFORMATION: miR-827

<400> SEQUENCE: 42
ttagatgacc atcagcaaac a                                              21

<210> SEQ ID NO 43
<211> LENGTH: 20
<212> TYPE: DNA
<213> ORGANISM: Artificial Sequence
<220> FEATURE:
<223> OTHER INFORMATION: miR-9470

<400> SEQUENCE: 43
tttggctcat ggattttagc                                                20

<210> SEQ ID NO 44
<211> LENGTH: 21
<212> TYPE: DNA
<213> ORGANISM: Artificial Sequence
<220> FEATURE:
<223> OTHER INFORMATION: miR-9476

<400> SEQUENCE: 44
aaaaagatgc aggactagac c                                              21
```

METHOD FOR MODULATING PLANT PROCESSES

TECHNICAL FIELD

The present invention relates to a method for modulating plant processes said method being characterized in that a plant is fed with an eco-friendly, biostimulant composition comprising plant and/or algae-derived exogenous small RNA molecules. In particular, the method of the invention can be used for modulating physiological or pathological plant processes, such plant growth, plant productivity, fruit quality, quality of produce, plant yield, plant response to abiotic stress and plant resistance to diseases or to infections.

BACKGROUND ART

Promoting plant growth and productivity is important in agriculture. Nowadays, these processes are mainly managed using fertilizers, plant growth substances such as hormones, physical modifications of the soil, etc.

However, the use of these agro-chemicals has resulted in many long-term environmental consequences such as resource depletion, environmental damages, and health effects.

In order to limit the use of environmentally dangerous chemical inputs, to increase crop yield, and promote plant growth and nutrient uptake, many efforts have been put towards the development and the implementation of ecologically sound approaches, based on natural products. Currently, in particular, biostimulants are attracting the interest of the business and research communities in agriculture.

Biostimulants are materials, other than fertilizers, that promote plant growth when they are applied in small quantities (Khan, et al 2009, JPlantGrowthRegul, 28:386-399). According to a more recent definition, plant biostimulants are substances and materials, with the exception of nutrients and pesticides, which when applied to plants, seeds or growing substrates in specific formulations, have the capacity to modify physiological processes of plants in a way that provides potential benefits to growth, development and/or stress response (Du Jardin P 2012, The Science of Plant Biostimulants).

In this contest, it is a primary object of the present invention to provide an eco-friendly method for modulating physiological or pathological plant processes, in particular, for improving plant growth, plant productivity, fruit quality, quality of produce, plant yield, plant response to abiotic stress and plant resistance to diseases or to infections.

DISCLOSURE OF THE INVENTION

In a first aspect, the present invention refers to an eco-friendly plant-derived biostimulant composition, preferably a plant extract and/or a plant exudate, comprising exogenous small RNA molecules and its use for modulating, in general, physiological or pathological plant processes, wherein the exogenous small RNA molecules are naturally derived from plants or parts of plants, such as roots, leaves, stem or any other part of plants.

Alternatively, the composition is algal-derived and therefore it comprises exogenous small RNA molecules naturally derived from algae.

In the context of the present invention, "small RNA molecules naturally derived from plants/algae" means that the molecules are naturally produced by said plants/algae, or that the molecules used are identical to the one produced in nature by said plants/algae.

In some embodiments of the invention, the biostimulant composition comprises exogenous small RNA molecules naturally derived from plants or plant parts and exogenous small RNA molecules naturally derived from algae.

Therefore, it is an object of the present invention a method for modulating physiological and/or pathological plant processes comprising at least one step of feeding a plant, also a growing plant or a seed, with a biostimulant composition comprising at least one exogenous small RNA molecule naturally derived from plants or plant parts and/or at least one exogenous small RNA molecule naturally derived from algae. In particular, the composition of the invention can be used for improving plant growth, plant productivity, fruit quality, quality of produce, plant yield, plant response to abiotic stress and plant resistance to diseases or to infections.

A preferred plant biostimulant composition comprises an exogenously applied single- and/or double-stranded RNAs, such as microRNAs, naturally derived from plants or from part of plants.

A further preferred plant biostimulant composition comprises of an exogenously applied single- and/or double-stranded RNAs, such as microRNAs, naturally derived from algae.

Preferably, the algae are macroalgae or microalgae more preferably are seaweeds.

In fact, Applicant has unexpectedly found that:
1) Small RNA molecules, such as miRNAs, are extremely stable in plant extracts/plant exudates;
2) Small RNA molecules, such as miRNAs, are extremely stable in algal extracts/algal lysates;
3) By feeding the plants to be treated with the compositions of the invention, the exogenous plant-derived small RNAs (derived from external plants and not produced by the treated plant itself) are able to reach the cells of the treated plants, and to modulate several biological processes of agricultural interest through gene-targeting mediated by an environmental RNA interference mechanism; and
4) Small RNA molecules extracted from algae include sequences that are highly conserved in plants. Therefore, it is very plausible that algae-derived small RNA molecules, preferably miRNAs, when used to feed a plant to be treated, are able to modulate biological processes of agricultural interest through gene-targeting mediated by an environmental RNA interference mechanism.

Therefore, by enriching the compositions with specific exogenous plant- and/or algae-derived small RNAs, it is possible to target (and therefore modulate) several specific gene functions in plants, such as the growth and the productivity of plants, the transition phase from the juvenile to the plant, and the response of plants to abiotic stress. Moreover, in this way, it is possible to leverage this use, for example, to increase plant yield and fruit and/or flower quality, to improve nutrient uptake, or plant resistance to specific disease caused for example by fungi, bacteria, viruses, or infestation by insects or nematodes.

Advantageously the method of the present invention is environmentally friendly and therefore safer compared to the agro-chemical products, such as plant growth regulators or pesticides, used at present for the same purpose.

DETAILED DESCRIPTION OF THE INVENTION

Figure 1:
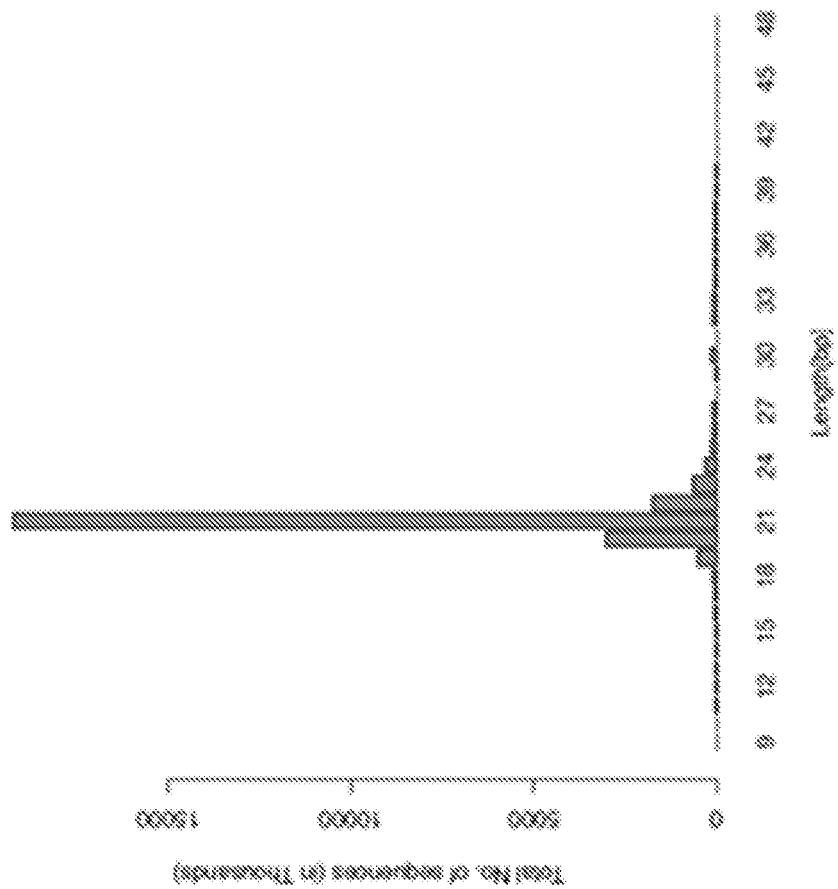
FIG. 1 shows the distribution of the small RNA sequence length in *Ascophyllum nodosum*.

For further understanding of the object, construction, characteristics and functions of the invention, a detailed description with reference to the embodiments is given below. In overall concept, the present invention, therefore discloses a method for modulating physiological and/or pathological plant processes comprising a step of feeding a plant with an eco-friendly biostimulant composition comprising at least one exogenous small RNA molecule naturally derived from (naturally produced by) at least one plant or a part of plants such as roots, leaves, stem or any other part of plants. Alternatively, the plant is fed with a biostimulant composition comprising at least one exogenous small RNA molecule naturally derived from (naturally produced by) algae.

According to a preferred embodiment of the invention, the biostimulant composition comprises at least one exogenous small RNA molecule naturally derived from at least one plant or plant part or plant exudate and at least one exogenous small RNA molecule naturally derived from algae.

In a preferred embodiment of the invention, the algae are macroalgae and/or microalgae, more preferably they are seaweeds.

In a preferred embodiment of the invention, the plants and/or algae are collected from natural sources or they are cultivated artificially.

According to a preferred embodiment of the invention, at least one exogenous small RNA molecule is derived from at least one extract or at least one exudate or any other sample of at least one plant or a part of a plant, such as roots, leaves, stem or any other part of plants.

According to a further preferred embodiment of the invention, the at least one exogenous small RNA molecule is derived from at least one extract or lysate of algae and/or microalgae, preferably of seaweeds, more preferably of brown seaweeds.

According to a preferred embodiment of the invention, the seaweed is selected from the group consisting of: *Ascophyllum nodosum*, *Ecklonia maxima*, *Laminaria saccharina*, *Fucus serratus*, *F. vesiculosus*, *Macrocystis* spp., and *Sargassum* spp.

For the purpose of the present invention, the preferred brown seaweed is *Ascophyllum nodosum*.

According to a preferred embodiment of the invention, the microalgae belong to the genus selected from the group consisting of: *Spirulina*, *Scenedesmus*, *Nannochloropsis*, *Haematococcus*, *Chlorella* and *Dunaliella*.

As used herein, the phrase "modulating physiological and/or pathological plant processes" refers to a process of modifying the expression of one or more genes responsible or involved in the plant process of interest, by down-regulating and/or up-regulating the expression of the genes through a mechanism involving the interference of the exogenous small RNA molecules (contained in the claimed composition and administered to the plant by feeding it) and the gene(s) of interest (environmental RNA interference, see below).

The composition of the invention can be used also to feed a growing plant or a seed.

As used herein, the physiological and/or pathological plant processes of interest refer, for example, to nutrient uptake, abiotic stress tolerance, growth and developmental processes such as flowering and fruit production, plant productivity in terms of quantity and quality, plant resistance to specific disease caused for example by fungi, bacteria, viruses, or infestation by insects or nematodes.

As used herein, the term "biostimulant/biostimulation" refers to plant growth promoting materials, other than fertilizers, usually used in small quantities. In other words, plant biostimulants are substances/materials, with the exception of nutrients and pesticides, which when applied to plants, seeds or growing substrate in specific formulations, have the capacity to modify physiological processes of plants in a way that provides potential benefits to growth, development and/or stress response. Thus, the application of biostimulants has a positive impact on plant nutrition and plant growth, while at the same time providing anti-stress effects. In view of the definition disclosed above, the composition used in the method of the invention can be considered a "biostimulant composition". In fact, when fed to plants for example, it is able to modify plant processes in a way that provides multiple benefits to plants; for example, it improves plant growth, plant development and/or plant response to stress.

As used herein, "small RNA molecules" mean short single/double-stranded RNA molecules, such as microRNAs (miRNAs) or small interfering RNAs (siRNAs), which are able to regulate gene expression by interfering with the messenger RNAs (mRNAs) or by other mechanisms of post-transcriptional gene silencing. The exogenous small RNAs, preferably the exogenous double-stranded RNAs, more preferably the exogenous miRNAs or siRNAs can be natural or artificial molecules. Therefore, the small RNA molecule is preferably obtained from a natural source, preferably a plant, more preferably a natural plant or a transgenic plant (genetically engineered plant).

Alternatively, the source from which the small RNA molecule is obtained is natural and/or transgenic algae or microalgae, preferably seaweeds, more preferably brown seaweeds. Preferably, the seaweeds are selected from the group consisting of: *Ascophyllum nodosum, Ecklonia maxima, Laminaria saccharina, Fucus serratus, F. vesiculosus, Macrocystis* spp., and *Sargassum* spp.

Preferably, the microalgae belong to the genus selected from the group consisting of: *Spirulina, Scenedesmus, Nannochloropsis, Haematococcus, Chlorella* and *Dunaliella*.

According to a preferred embodiment, the small RNA molecules used in this invention may be synthesized artificially. In this context artificial molecule means a molecule synthesized in the laboratory, in other words an artificial molecule is a synthetic molecule. Therefore, in a preferred embodiment of the invention the composition administered to the plants in the method of this invention comprises artificial exogenous small RNAs, preferably artificial exogenous double-stranded RNAs, and more preferably artificial exogenous miRNAs. In any case, the sequence of these small RNA molecules, preferably miRNAs, are identical or very similar to the sequence of the small RNA naturally present in plants and/or algae.

According to a preferred embodiment the small RNA molecule is selected from: miR156, miR399d, miR166, miR398, miR168, miR396, miR159, miR6027, miR6024, miR162, miR157, miR9471, miR390, miR169, miR1919, miR397, miR414, miR4376, miR482, miR5168, miR5300, miR827, miR9470, miR9476, more preferably is miR156 and/or miR399d.

According to a further preferred embodiment, said small RNA molecules comprise a sequence selected from: SEQ ID NO: 1-44.

As used herein, "RNA interference (RNAi)" refers to an endogenous post-transcriptional genetic regulatory mechanism generally mediated by non-coding RNA molecules (siRNAs/miRNAs). In particular, this mechanism can be utilized for targeted gene silencing by introduction of nucleic acid based tools that are specially designed to trigger the RNAi mechanism.

Following the discovery of RNAi, several potential applications have been proposed. In the plant/crop area, for example, the use of RNAi as a tool for modulating plant physiology is nowadays a commonly used technique. In particular, this method is a transgenic approach by which a plant overexpresses a miRNA or another small RNA sequence in order to silence the expression of the target gene(s). However, the present invention is based on the concept of horizontal transfer of genetic material, specifically miRNAs or other small RNAs able to trigger RNAi. This process is also named "environmental RNA interference", meaning that, besides controlling gene expression by multiple mechanisms within a cell producing them or systemically in the plant producing them, RNA molecules can be exported, through an unknown mechanism, outside the plant as well into other plants wherein they modulate physiological and/or pathological processes by interfering with the gene expression.

Thus, according to the present invention, it is possible to feed a plant (or a seedling or a seed or even a primordial plant tissue) with a composition comprising at least one exogenous small RNA molecule, preferably at least one double-stranded RNAs such as miRNA molecules, wherein this exogenous molecule is naturally derived from plants or plant parts and/or from algae and/or from microalgae and wherein this exogenous molecule is able to modulate the expression of one or more plant genes involved in a plant process, through an environmental RNA interference mechanism. This means that the small RNA molecules used in the method of the invention are molecules naturally present in plants/algae and they derived from an extract of plants/plant parts/algae or from an exudate of plants/plant parts and they are used for modulating physiological and/or pathological processes of other plants not producing them.

More preferably, at least one exogenous small RNA molecule is involved in modulating the specific plant process of interest. In other words, the composition of the invention preferably contains at least one exogenous small RNA molecule (derived from plants and/or plant parts and/or from algae and/or from microalgae) able to modulate (suppressing or overexpressing) the expression of the gene of interest through an environmental RNA interference mechanism and therefore to modulate (enhancing or impairing) the plant process of interest.

Alternatively, the composition comprises an extract, an exudate, any sample derived from plants or part of plants, such as roots or leaves, wherein said extract, exudate or sample comprises (plant-derived) exogenous small RNA molecules, preferably double-stranded RNAs such as miRNAs.

According to a preferred embodiment the miRNA is selected from: miR156, miR399d, miR166, miR398, miR168, miR396, miR159, miR6027, miR6024, miR162, miR157, miR9471, miR390, miR169, miR1919, miR397, miR414, miR4376, miR482, miR5168, miR5300, miR827, miR9470, miR9476 or combination thereof, more preferably is miR156 and/or miR399d.

According to a further preferred embodiment, the miRNA comprises a sequence selected from: SEQ ID NO: 1-44.

According to a preferred embodiment of the invention, the small RNAs, preferably the double-stranded RNAs such as miRNA molecules, derived from a plant selected from the group consisting of: Sugar beet (*Beta vulgaris*), Sugar cane (*Saccharum officinarum*), Corn (*Zea mays*) and Alfalfa (*Medicago sativa*).

However, any plant, dicotyledonous or monocotyledonous or part or mixtures thereof can be used for the scope of the present invention.

The plant, from which the exogenous small RNAs of the composition used in the method of the invention are derived, can be a wild type or a genetically modified plant, such as a plant genetically modified in order to express the small RNAs of interest, preferably the double-stranded RNAs of interest, more preferably the miRNAs of interest.

According to a further embodiment of the invention the composition comprises an extract or a lysate or any sample derived from algae and/or microalgae, preferably from seaweeds, more preferably from brown seaweeds, preferably a seaweed selected from the group consisting of: *Ascophyllum nodosum, Ecklonia maxima, Laminaria saccharina, Fucus serratus, F. vesiculosus, Macrocystis* spp., and *Sargassum* spp. wherein said extract, lysate or sample comprises (algal-derived) exogenous small RNA molecules, preferably double-stranded RNAs such as miRNAs. Preferably, the microalgae belong to the genus selected from the group consisting of: *Spirulina, Scenedesmus, Nannochloropsis, Haematococcus, Chlorella* and *Dunaliella*.

Another preferred embodiment of the composition of this invention comprises components such as substances able to modify the surface tension, surfactants, adjuvants, adhesives or wetting agents and substances able to facilitate transport of the composition inside the plant towards the target sites.

According to a further embodiment, the composition of the invention further comprises micronutrients and/or macronutrients.

Examples of useful micronutrients are: KCl, $H_3BO_3$, $MnSO_4$, $CuSO_4$, $ZnSO_4$, or Fe-EDTA.

Examples of useful macronutrients are: KNOB, Ca $(NO_3)_2$, $MgSO_4$, $KH_2PO_4$.

Preferably, the micronutrients are present in a concentration ranging from 0.1 to 20% w/w, preferably from 1 to 10% w/w, more preferably from 2 to 6% w/w.

Preferably, the micronutrients are present in a concentration ranging from 0.01-100 mg/Kg for the single application (when applied).

Preferably, the macronutrients are present in a concentration ranging from 0.5 to 50% w/w, preferably from 10 to 30% w/w, more preferably from 12 to 25% w/w.

Preferably, the macronutrients are present in a concentration ranging from 1-50 grams/Kg for the single application (when applied).

In a further preferred embodiment of the invention, the biostimulant composition can be administered as powder, preferably water-soluble powder, granules, gel, tablets, emulsion, emulsifiable concentrate, or as a liquid solution (a medium) or a liquid suspension. More preferably, the composition can be diluted or undiluted before being administered.

In a further embodiment of the invention, the composition can be applied to plants in any way. Preferably, the plants can be fed with the disclosed composition through root as a soil-applied product or leaves as a foliar treatment.

The composition is preferably formulated as a spray when it is administered through the leaves.

Preferred embodiments of the invention do not preclude applying the method here disclosed in combination with compositions comprising chemicals, such as fertilizers, other biostimulants, hormones, plant growth regulators (PGR), Plant Growth Promoting Rhizobacteria (PGPR), pesticides or any other substances known to be used on plants for the same purpose. These combinations are particularly useful in order for reducing the rates or per-season application doses of said fertilizers, biostimulants, hormones, PGRs, PGPR, pesticides or any compound synergizes or inhibits the activity of these compounds, thus reducing the adverse effects on the environment.

The use of the compositions of the present invention (the method of the invention) is an eco-friendly alternative to the current chemicals available on the market for the purpose of modulating plant processes, such as improving plant productivity or plant growth. In fact, the use of the composition here disclosed could reduce the ecological impact of treating plants with harmful chemicals such as herbicides and pesticides. Therefore, the use of the compositions of the present invention is environmentally and biologically safe.

Following the present invention is exemplified in order to better illustrate and not to limit the invention.

Example I

Extraction and Characterization of the *Ascophyllum Nodosum* miRNAs

*Ascophyllum nodosum* small RNA was extracted by 100 mg of algae samples (previously stored at −80° C.) with mirPremier microRNA Isolation Kit (Sigma-Aldrich).

Purified small RNA samples were analyzed by 4% agarose gel electrophoresis and the quality was checked by a BioAnalyser.

Since most of the mature miRNAs have a 3'-hydroxyl group as a result of the enzymatic cleavage by Dicer or other RNA processing enzymes, we used the TruSeq Small RNA Sample Preparation Kit (Illumina) to prepare a miRNA library. This technology uses a 3' adapter specifically modified to target microRNAs and other small RNAs that have a 3' hydroxyl group. Next, the isolated miRNA were sequenced using the HiSeq 2000 platform (IGA Technology Service, Udine).

The obtained sequences were then cleaned removing adaptor/acceptor sequences. A total of 27,152,631 reads was obtained that produced 2,117,202 unique miRNA. The occurrence of the length of the total number of sequence reads was counted, considering only the range from 9 to 48 nucleotides, showing that the majority of the small RNA from *Ascophyllum* library was 21 in size (FIG. 1), that is consistent with the typical miRNA size produced by Dicer.

The putative miRNA sequences identified were compared to known miRNA using the miRBase database.

Figure 2:
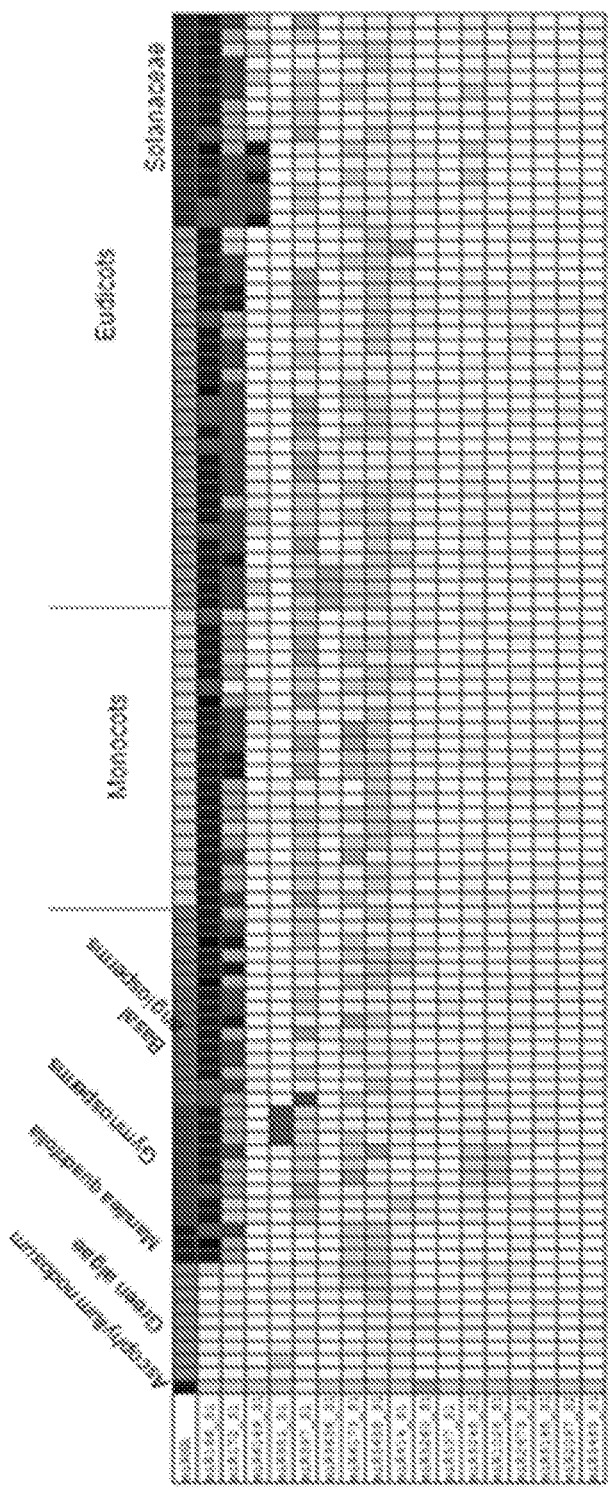
FIG. 2 shows the miRNA families identified by comparing the mRNA identified in *Ascophyllum nodosum* and the known miRNAs.

With this analysis, 316 known miRNA families were identified, thus composed by miRNA orthologs from other plant species. Among them, 17 miRNA families have a relatively more sequence counts (10<n<106), indicating that probably they are highly expressed (FIG. 2).

Figure 3:
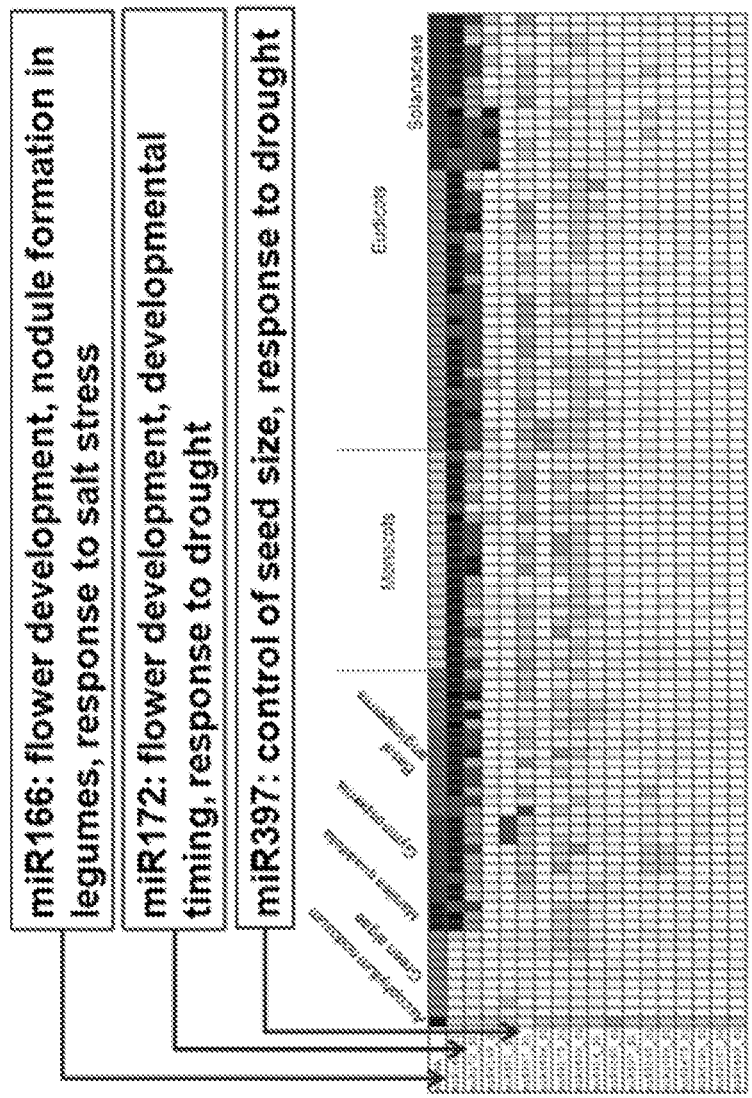
FIG. 3 shows examples of miRNAs identified in *Ascophyllum nodosum* and their role in higher plants.

Some of them are involved in regulation of processes regarding plant development and stress response (FIG. 3).

The miRNA sequences comprehending 20-22 nucleotides and repeated at least 100 times (5,059 sequences) were blasted against the *Arabidopsis* NCBI GenBank database to find possible targets. The results reported the possible Ascophyllum miRNA sequence match with 2,303 annotated *Arabidopsis* genes. This group possibly comprehends also novel miRNA not represented in previously known miRNA family. The matched *Arabidopsis* genes were grouped in 50 classes involved in Biological Processes (52%), Molecular Functions (44%) and Cellular Components (4%) (GO classification—FIG. 4).

Figure 4:
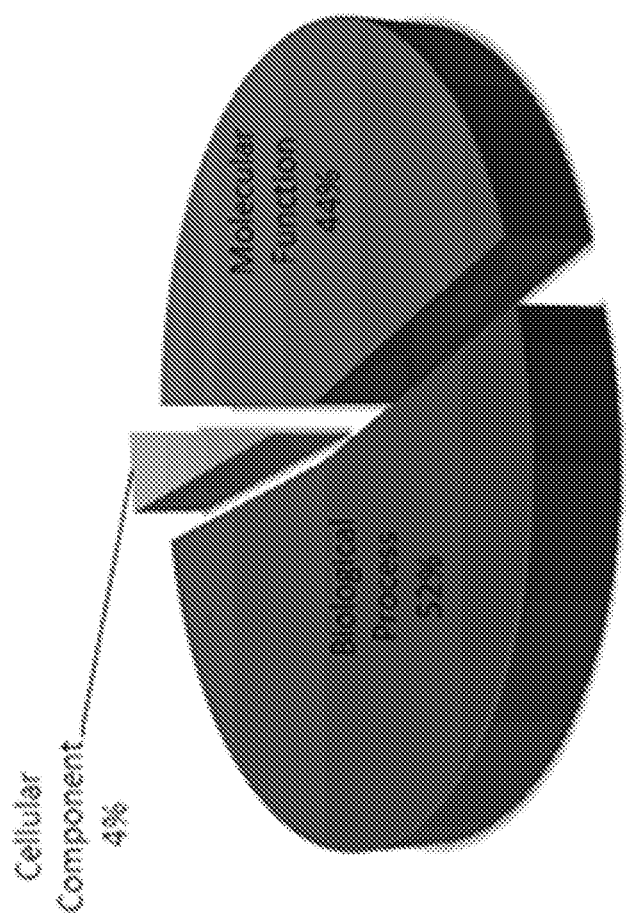
FIG. 4 shows the Gene Ontology (GO) classification of the putative targets of the miRNAs identified in *Ascophyllum nodosum*.

The targets related to the Biological Process GO:0007166 (p=6.08E-05) comprehend genes related to defense mechanism activation, response to cold, response to ethylene, ABA and sugar stimuli, hormones and carbohydrate metabolisms, growth and development (FIG. 4). This group of *Arabidopsis* genes is likely an interesting target for the action of the miRNAs produced by *Ascophyllum nodosum*.

*Ascophyllum nodosum* miRNAs are Highly Conserved in Plants

To identify the conserved miRNA in *Ascophyllum nodosum*, we compared the dataset with the known plants and animals miRNAs using the miRBase database (version 21, released on 2014 06, http://www.mirbase.org).

Allowing no mismatches between sequences of 20-22 nucleotides, a total of 62 putative mature miRNAs were identified corresponding to known plants miRNA families (Table II), thus composed by putative miRNA orthologues of different plant species.

Table II shows sequences identified in *Ascophyllum nodosum* sharing 100% homology with the sequence of known miRNAs for higher plants.

TABLE II

| Name | Sequences | SEQ ID | ID codes used for identifying the family |
|---|---|---|---|
| miR-166 | AGAATGTCGTCTGGTTCGAGA | SEQ ID NO: 1 | miR166, miR166a, miR166a-3p, miR166b, miR166c, miR166c-3p, miR166c-5p, miR166d, miR166d-3p, miR166d-5p, miR166e, miR166e-3p, miR166f, miR166f-3p, miR166g, miR166g-3p, miR166h, miR166h-3p, miR166i, miR166i-3p, miR166i-5p, miR166j, miR166j-3p, miR166k, miR166k-3p, miR166l, miR166l-3p, miR166m, miR166n, miR166n-3p, miR166o, miR166p, miR166q, mir166r, mir166s, mir166t, miR166u |
| | GGGATGTTGTCTGGCTCGACA | SEQ ID NO: 2 | |
| | TCGGACCAGGCTTCAATCCCT | SEQ ID NO: 3 | |
| | TCGGACCAGGCTTCATTC | SEQ ID NO: 4 | |
| | TCGGACCAGGCTTCATTCC | SEQ ID NO: 5 | |
| | TCGGACCAGGCTTCATTCCCC | SEQ ID NO: 6 | |
| | TCGGACCAGGCTTCATTCCCT | SEQ ID NO: 7 | |
| | TCGGACCAGGCTTCATTCCTC | SEQ ID NO: 8 | |
| | TCTCGGACCAGGCTTCATTCC | SEQ ID NO: 9 | |
| | TTGGACCAGGCTTCATTCCCC | SEQ ID NO: 10 | |
| miR-398 | GGGTTGATTTGAGAACATATG | SEQ ID NO: 11 | miR398: miR398a, miR398a-3p |
| | TATGTTCTCAGGTCGCCCCTG | SEQ ID NO: 12 | |
| miR-168 | CCCGCCTTGCATCAACTGAAT | SEQ ID NO: 13 | miR-168: miR168a, miR168a-3p, miR168a-5p, miR168b, miR168b-3p, miR168b-5p, miR168c, miR168c-5p, miR168d, miR168e |
| | CCTGCCTTGCATCAACTGAAT | SEQ ID NO: 14 | |
| | TCCCGCCTTGCACCAAGTGAAT | SEQ ID NO: 15 | |
| | TCGCTTGGTGCAGATCGGGAC | SEQ ID NO: 16 | |
| | TCGCTTGGTGCAGGTCGGGAC | SEQ ID NO: 17 | |
| miR-396 | GTTCAATAAAGCTGTGGGAAG | SEQ ID NO: 18 | miR396: miR396c, miR396c-3p, miR396c-5p, miR396d, miR396d-3p, miR396d-5p, miR396e, miR396e-3p, miR396e-5p, miR396f, miR396f-5p, miR396h, miR396i-5p, miR396k-5p |
| | TTCCACAGCTTTCTTGAACTT | SEQ ID NO: 19 | |
| miR-159 | TTTGGATTGAAGGGAGCTCTA | SEQ ID NO: 20 | miR159: miR159, miR159a, miR159a.1, miR159a-3p, miR159b, miR159b-3p.1, miR159c, miR159d, miR159f, miR159f-3p, miR159j-3p, mir159k-3p |
| miR-6027 | ATGGGTAGCACAAGGATTAATG | SEQ ID NO: 21 | miR6027: miR6027, miR6027-3p, miR6027-5p |
| | TGAATCCTTCGGCTATCCATAA | SEQ ID NO: 22 | |
| miR-6024 | TTTAGCAAGAGTTGTTTTACC | SEQ ID NO: 23 | miR6024: miR6024 |
| | TTTTAGCAAGAGTTGTTTTACC | SEQ ID NO: 24 | |
| miR-162 | TCGATAAACCTCTGCATCCAG | SEQ ID NO: 25 | miR162: miR162, miR162-3p, miR162a, miR162a-3p, miR162b-3p, miR162c |
| miR-156 | GCTTACTCTCTATCTGTCACC | SEQ ID NO: 26 | miR156: miR156a, miR156aa, miR156b, miR156c-3p, miR156e-3p, miR156f, miR156g, miR156g-3p, miR156h, miR156i, miR156j, miR156p, miR156q, miR156r, miR156s, miR156x, miR156y, miR156z |
| | TTGACAGAAGATAGAGAGCAC | SEQ ID NO: 27 | |
| miR-157 | TTGACAGAAGATAGAGAGCAC | SEQ ID NO: 28 | miR157: mIr157d, miR157d-5p |
| miR-9471 | TTGGCTGAGTGAGCATCACGG | SEQ ID NO: 29 | miR9471: miR9471a-3p, miR9471b-3p |
| | TTGGCTGAGTGAGCATCACT | SEQ ID NO: 30 | |
| | TTGGCTGAGTGAGCATCACTG | SEQ ID NO: 31 | |
| miR-390 | AAGCTCAGGAGGGATAGCACC | SEQ ID NO: 32 | miR390: miR390, miR390-5p, miR390a, miR390a-5p, miR390b-5p, miR390c, miR390d, miR390d-5p, |
| | AAGCTCAGGAGGGATAGCGCC | SEQ ID NO: 33 | |

TABLE II-continued

| Name | Sequences | SEQ ID | ID codes used for identifying the family |
|---|---|---|---|
| | | | miR390e, miR390f, miR390g |
| miR-169 | TAGCCAAGGATGACTTGCCT | SEQ ID NO: 34 | miR169: miR169, miR169a, miR169b, miR169c, miR169d, miR169e, miR169f, miR169g, miR169h, miR169i, miR169j, miR169k, miR169l, miR169m, miR169m, miR169o, miR169p, miR169q, miR169r, miR169s, miR169t, miR169u |
| miR-1919 | TGTCGCAGATGACTTTCGCCC | SEQ ID NO: 35 | miR1919, miR1919-5p, miR1919c-5p |
| miR-397 | ATTGAGTGCAGCGTTGATGAC | SEQ ID NO: 36 | miR397: miR397, miR397-5p, miR397a, miR397b-5p |
| miR-414 | TCATCCTCATCATCATCGTCC | SEQ ID NO: 37 | miR414: miR414 |
| miR-4376 | TACGCAGGAGAGATGATGCTG | SEQ ID NO: 38 | miR4376: miR4376, miR4376-5p |
| miR-482 | TCTTGCCTACACCGCCCATGCC | SEQ ID NO: 39 | miR482, miR482b-3p, miR482d |
| miR-5168 | TCGGACCAGGCTTCAATCCCT | SEQ ID NO: 40 | miR5168: miR5168-3p (blast with also miR166 family) |
| miR-5300 | TCCCCAGTCCAGGCATTCCAAC | SEQ ID NO: 41 | miR5300: miR5300 |
| miR-827 | TTAGATGACCATCAGCAAACA | SEQ ID NO: 42 | miR827: miR827, miR8273p |
| miR-9470 | TTTGGCTCATGGATTTTAGC | SEQ ID NO: 43 | miR9470: miR6471b-3p |
| miR-9476 | AAAAAGATGCAGGACTAGACC | SEQ ID NO: 44 | miR9476: miR9476-3p |

The results show that *Ascophyllum* extracts contain small RNAS whose sequences are identical to those expressed in higher plants as miRNAs. It is very plausible that these miRNAs are able to modulate physiological and/or pathological processes in plants by means of an environmental interference mechanism since they are highly conserved in plants.

Example II

Plant Release of miRNAs.

In order to verify if a plant is able to release miRNAs, a hydroponic system was used. In particular, *Arabidopsis* plants were grown in a growth chamber at 23° C. with a 12/12 photoperiod. The light intensity was 100 micromole photons m$^{-2}$ s$^{-2}$ (as described by Gibeaut et al. 1997, Plant Physiol., 115: 317-319) and miRNA399d was detected in the external growing medium.

The analysis has been carried out by using an RT-PCR methodology, coupled with the quantitative PCR detection of miR399d, pre-miR399d, the RNA sequences rRNA 40S and GAPDH.

Figure 5:
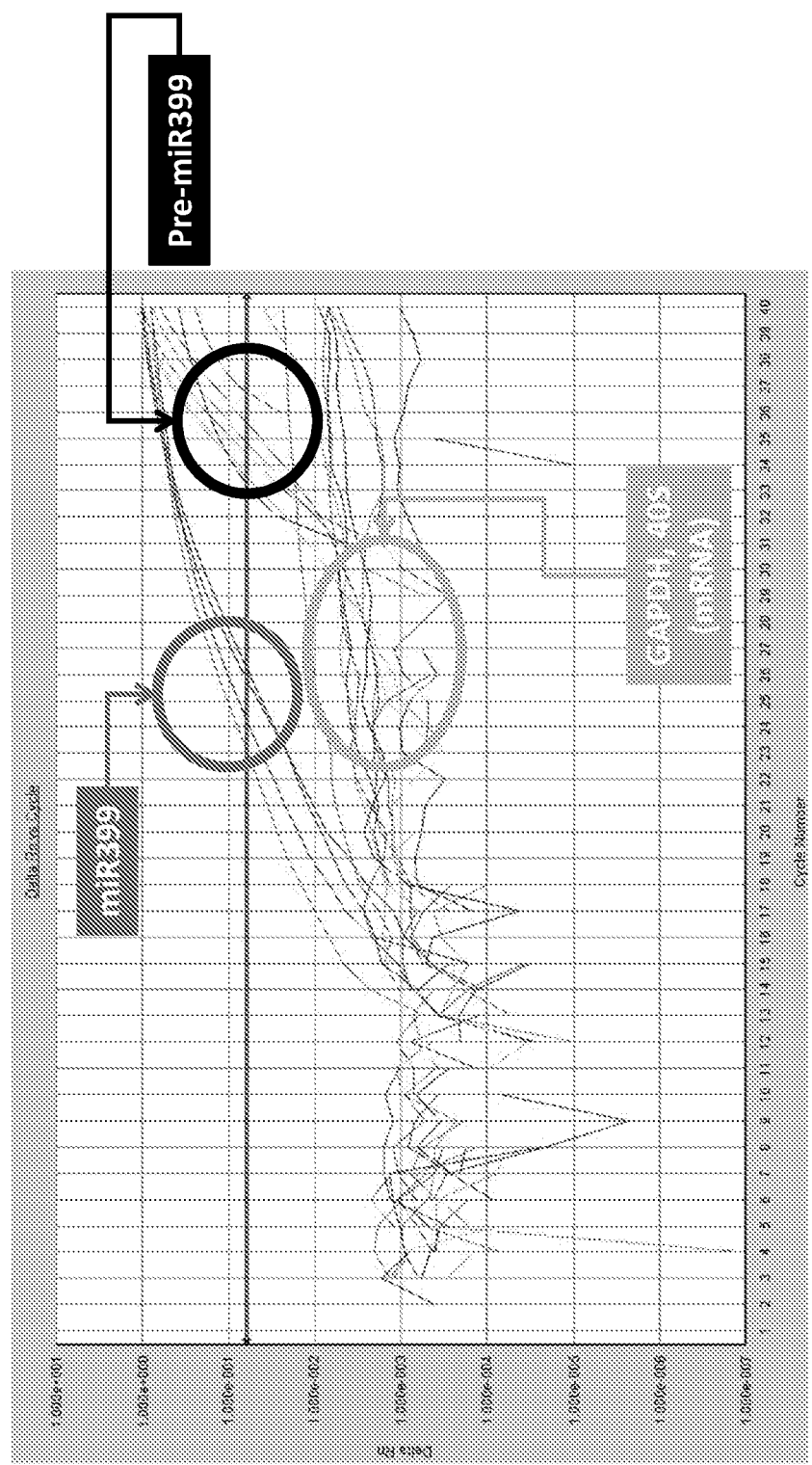
FIG. 5 shows RT-PCR analysis coupled with quantitative PCR detection of miR399d, pre-miR399d, and the mRNA sequences of rRNA 40S and GAPDH performed on the external growing medium of *Arabidopsis* plants grown using a hydroponic medium.

A stem-loop RT procedure followed by sybr-green PCR analysis was used to amplify the miR399 sequence. The results shown in FIG. 5 clearly show that pre-miR399 as well as the mature miR399 sequences was detected in the external growing medium, while the other, single-stranded RNA sequences were not detectable.

These results strongly suggest that miRNA can be released from *Arabidopsis* roots and they support the view of subsequent uptake of the miRNAs by neighboring plants. The detection of miRNAs in the non-sterile external hydroponic medium suggested that miRNAs are stable even outside the plant.

The Stability of miRNAs after Extraction.

It is generally thought that RNAs are highly unstable due to the action of RNases. In order to verify the stability of small RNAs molecules outside the cellular compartment, miRNAs stability has been evaluated in a crude plant extract.

Total RNA has been extracted from the shoots and the roots of *Arabidopsis* plants overexpressing miR399d. The leaves were rapidly frozen in liquid followed by extraction by grinding with mortar and pestle using 100 mM citrate buffer (pH 6).

The extract has been kept, without performing a centrifuging step, at room-temperature (RT) and at 4° C. for several days.

Figure 6:
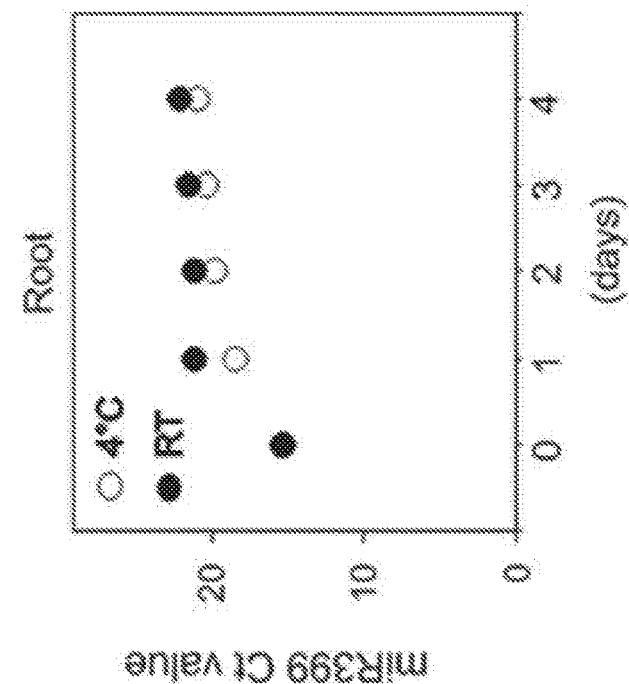
FIG. 6 shows the stability (at room temperature and at 4° C.) of miR399d following extraction of miRNAs in citrate buffer from the shoots (A) and from the roots (B) of *Arabidopsis* overexpressing miR399d.
Figure 6:
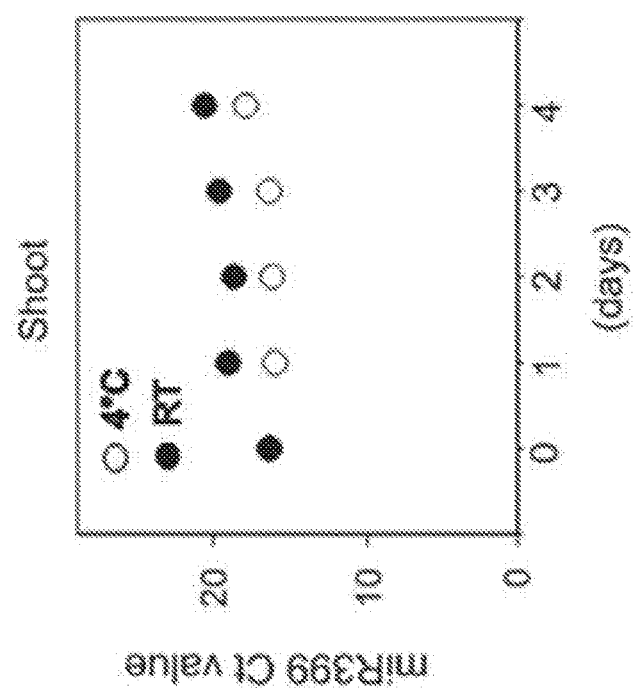

Unexpectedly, miR399d has been detected in the either root or shoot-derived extracts even after 4 days of incubation. No significant miR399d stability differences have been observed between RT or 4° C. conditions (FIG. 6).

These results demonstrate the stability of miRNAs in an extract and, therefore confirm the possibility to formulate a double stranded-RNA-based product to be fed exogenously to plants in order to modulate plant gene expression without any concerns relating to RNA stability.

Example III

Co-Cultivation of *Arabidopsis* Plants Overexpressing miR399d Results in Silencing of the Target Gene (PHO2) in Nearby Wild-Type Plants.

In order to understand if exogenous miRNAs can affect the expression of the target gene in a plant that is not the one producing it, we set-up an experiment in which wild-type *Arabidopsis* plants (FIG. 7A) and plants overexpressing the miR399d gene (OE-miR399d-FIG. 7B) were grown separately using a hydroponic system.

The composition of the hydroponic solution is reported in Table I.

TABLE I

| Macronutrients | |
| --- | --- |
| KNO3 | 1.25 mM |
| Ca(NO3)2 | 1.50 mM |
| MgSO4 | 0.75 mM |
| KH2PO4 | 0.50 mM |
| Micronutrients | |
| KCl | 50 µM |
| H3BO3 | 50 µM |
| MnSO4 | 10 µM |
| CuSO4 | 1.5 µM |
| ZnSO4 | 2 µM |
| Fe-EDTA | 72 µM |

Figure 7:
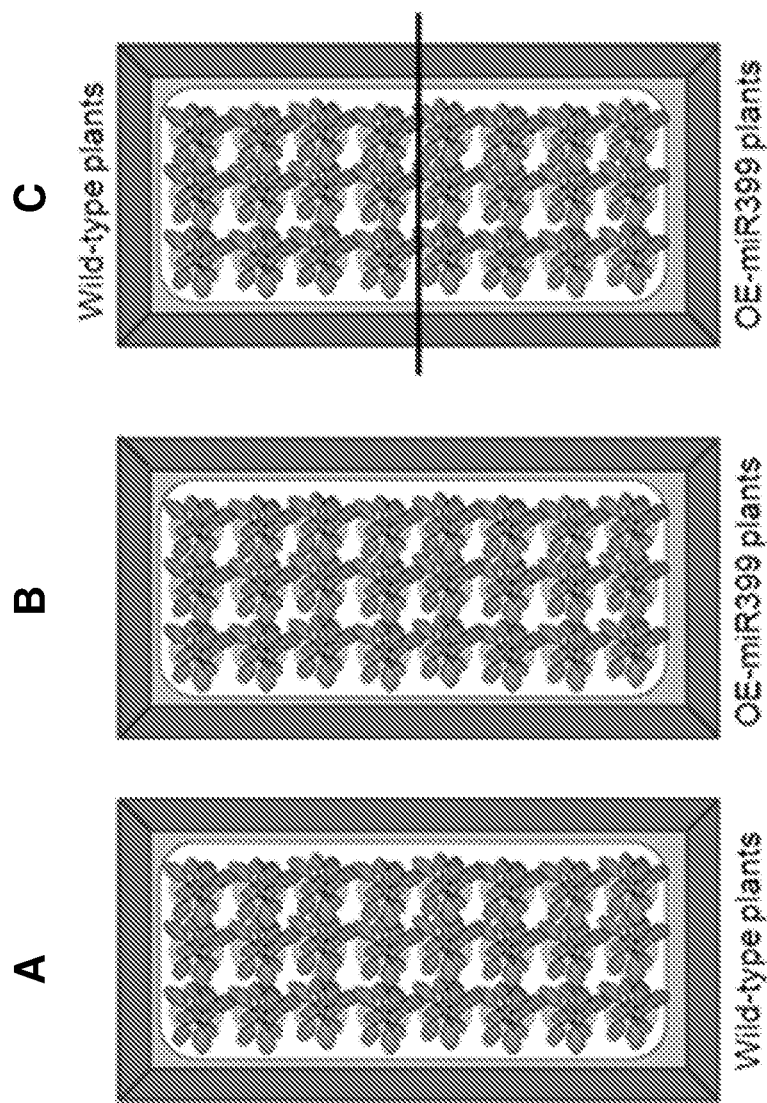
FIG. 7 shows the cultivation system used to verify the effect of miRNAs extracted from OE-miR399d plants (plants overexpressing miR399d) when exogenously fed to wild-type plants. 7A cultivation of wild type plants, 7B cultivation of OE-miR399d plants, and 7C co-cultivation of wild type and OE-miR399d plants.

A group of plants was co-cultivated in the same tray. Thus, the miRNAs eventually leaking from the OE-miR399d plants can reach the root system of the wild-type plants (FIG. 7C). Therefore, if the miRNAs produced by the OE-miR399d be taken-up by the wild-type plants, one should expect that the expression of the PHO2 gene, which is the target of miR399, to be affected also in the wild-type plants that were co-cultivated with the OE-miR399d plants.

Figure 8:
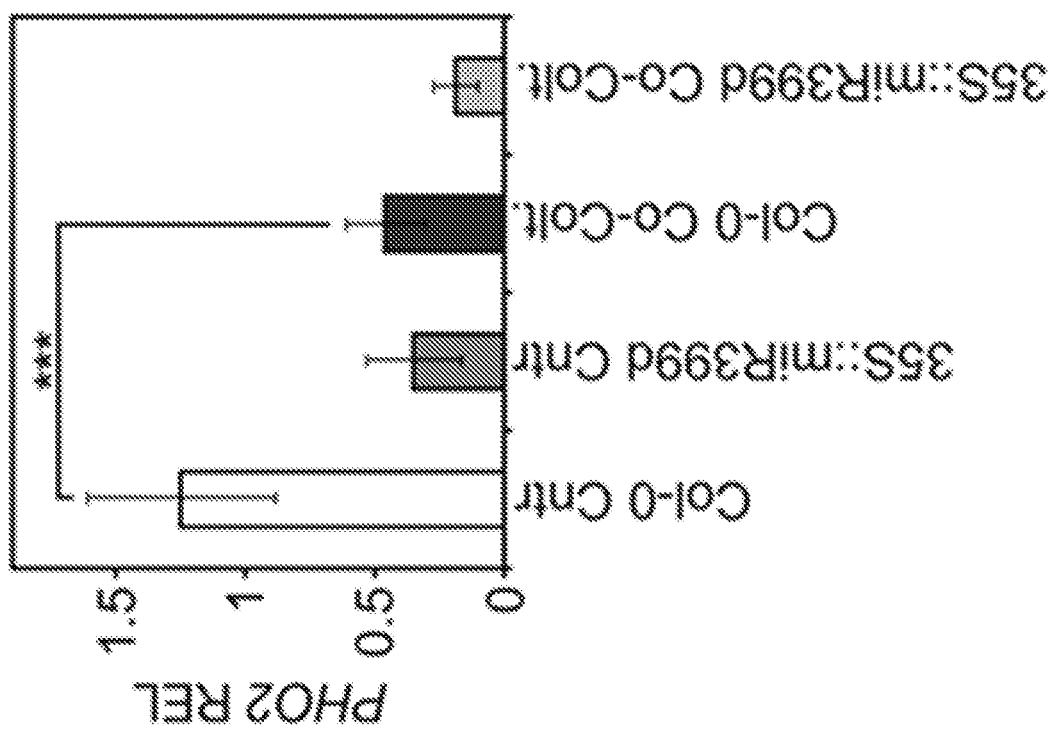
FIG. 8 shows the expression of PHO2 in wild-type plants (Col-O Cntr), in OE-miR399d plants (35S::miR399d Cntr), in wild-type plants co-cultivated with OE-miR399d plants (Col-O Co-Colt.) and in OE-miR399d plants co-cultivated with wild-type plants (35S::miR399d Co-Colt.).

The results showed that the expression of PHO2 has been reduced in the wild-type plants that were co-cultivated with the OE-miR399d plants, thus indicating that miRNAs leak out of the roots of OE-miR399d plants and are taken-up by wild-type plants (FIG. 8).

Since the expression of PHO2 is strongly affected by the phosphate level in the medium, the experiment was repeated adding extra-phosphate to the medium.

Figure 9:
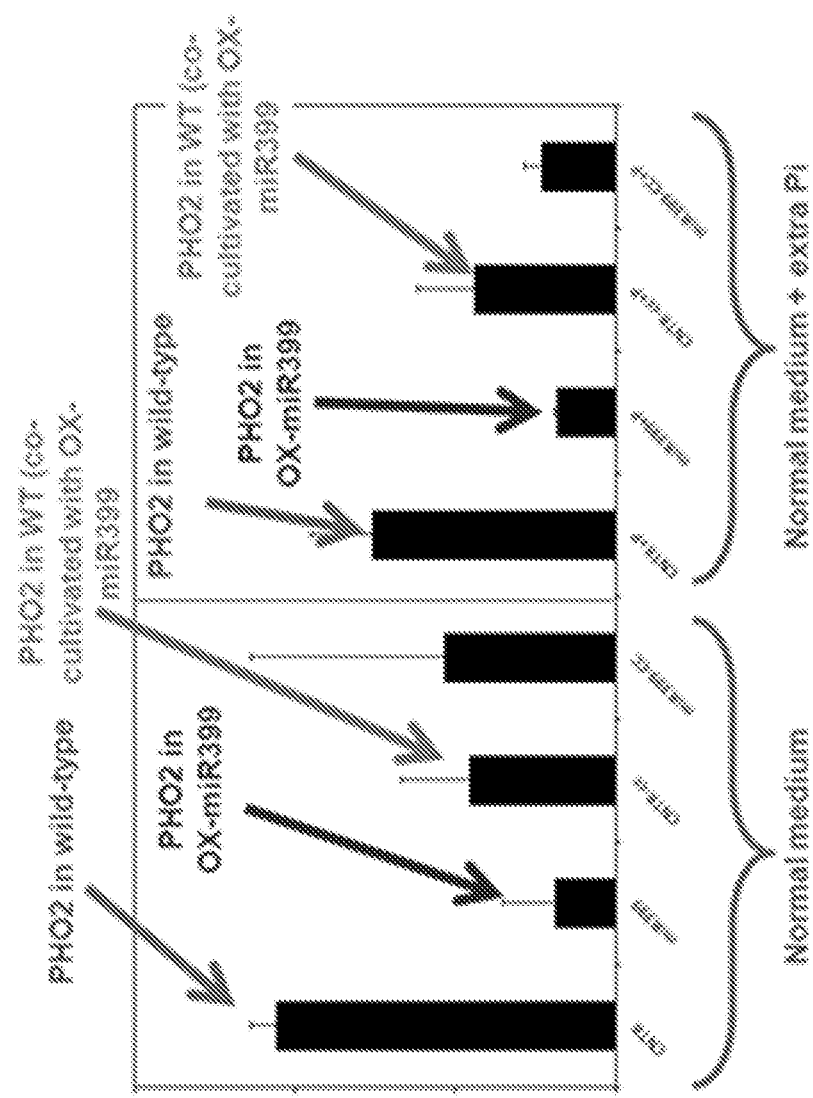
FIG. 9 shows the expression of PHO2 in wild-type plants (Cntr), in OE-miR399d plants (miR399), in wild-type plants co-cultivated with OE-miR399d plants (CNTR-cc), and in OE-miR399d plants co-cultivated with wild-type plants (miR399-CC) when the plants have been grown with a concentration of Pi of 3 mM (right graph) and 1.5 mM (left graph).

The results confirmed that the exogenous miRNA repressed PHO2 in the wild-type plants even in the presence of extra-phosphate in the medium (FIG. 9).

In a separate experiment, the wild-type plants were treated with a medium where either wild-type plants or OE-miR399d plants were cultivated since the germination stage. This medium should contain miRNAs leaked out respectively from the wild-type roots or the OE-miR399d roots.

Figure 10:
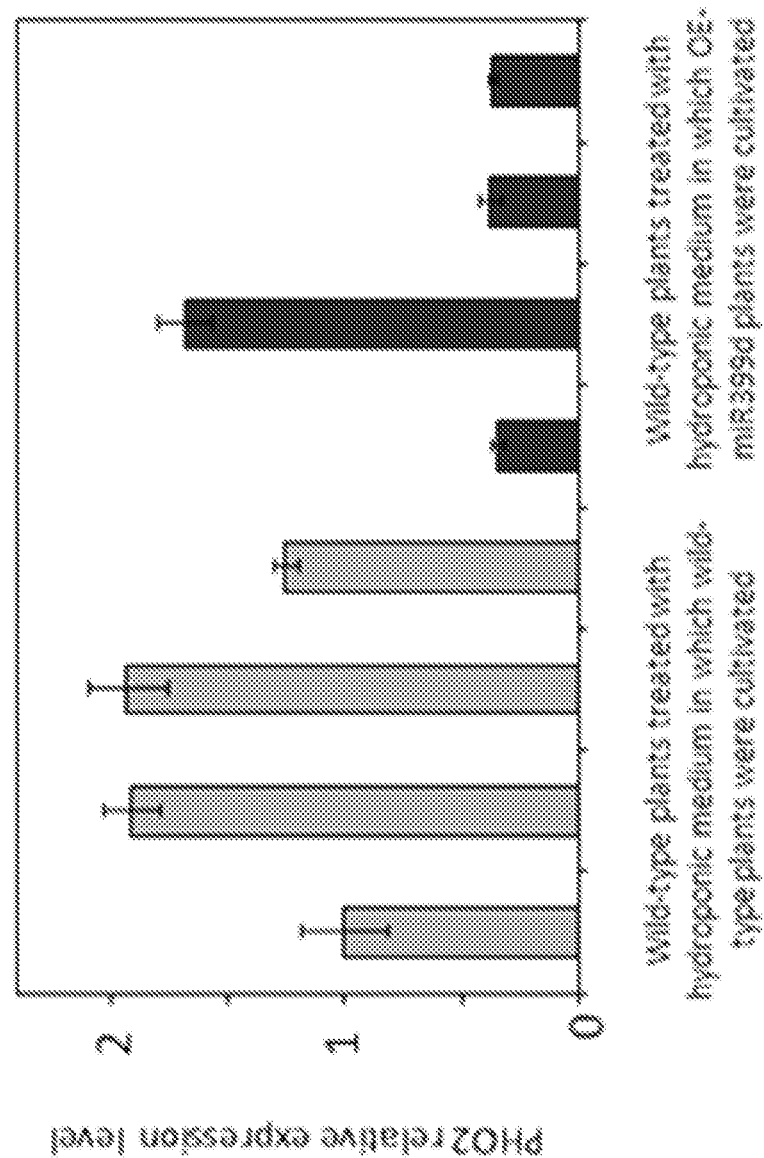
FIG. 10 shows the expression of PHO2 in wild-type plants treated with the medium where wild-type (light grey) and OE-miR399d were cultivated (dark grey).

The results in FIG. 10 show the expression of PHO2 in roots of four individual plants for each of the two treatments. In three out of four cases, the medium from OE-miR399d plants was able to repress PHO2 (FIG. 10).

Overall, these results confirm that exogenous miRNAs can modulate the expression of a target gene in the plant treated with a miRNA-containing solution.

These results also indicate that any extract, solution, product derived from a plant and containing exogenous miRNAs can affect the plant growth processes, including those associated with traits of agronomical importance.

A solution of miRNAs can be prepared from root exudates, from a plant extract or any other possible procedure that can provide a miRNA-containing product.

These miRNA/small RNA-containing products can be used to treat plants or plant organs by root feeding, leaf sprays or any other possible method that is used in agriculture to deliver fertilizers, PGRs, pesticides or any other product used on plants and crops.

Example IV

The following experiment demonstrates that a solution containing miRNAs resulting from exudation from roots of plants overexpressing a specific miRNA influences the expression of target genes in a plant exposed to the miRNA-enriched solution.

The miRNA system used is miR156/SPL9, where miR156 is able to repress the mRNA of the SPL9 gene, an activator of miR172. This regulatory cascade affects plant development, namely the transition from the juvenile phase to the adult phase, as well as the tolerance to abiotic stresses.

Wild-type plants and miR156 overexpressing plants were grown in Murashige-Skoog medium under sterile conditions.

In particular, the plants were grown in the medium for 5 days. Then, the medium was exchanged and the wild-type plants were transferred to the medium where the 35S::miR156 plants where previously grown and viceversa.

At this point, the treated plants were grown in the new medium for two additional days.

A set of plants was left in the original medium as a control.

The following Table IV summarizes the experimental set-up.

TABLE IV

| Sample | First 5 days | 48 h treatment |
| --- | --- | --- |
| A | Wild-type | Wild-type seedlings in Wild-type medium |
| B | 35S::miR156 | 35S::miR156 seedlings in 35S::miR156 medium |
| C | Wild-type | Wild-type seedlings in 35S::miR156 medium |
| D | 35S::miR156 | 35S::miR156 seedlings in Wild-type medium |

Figure 11:
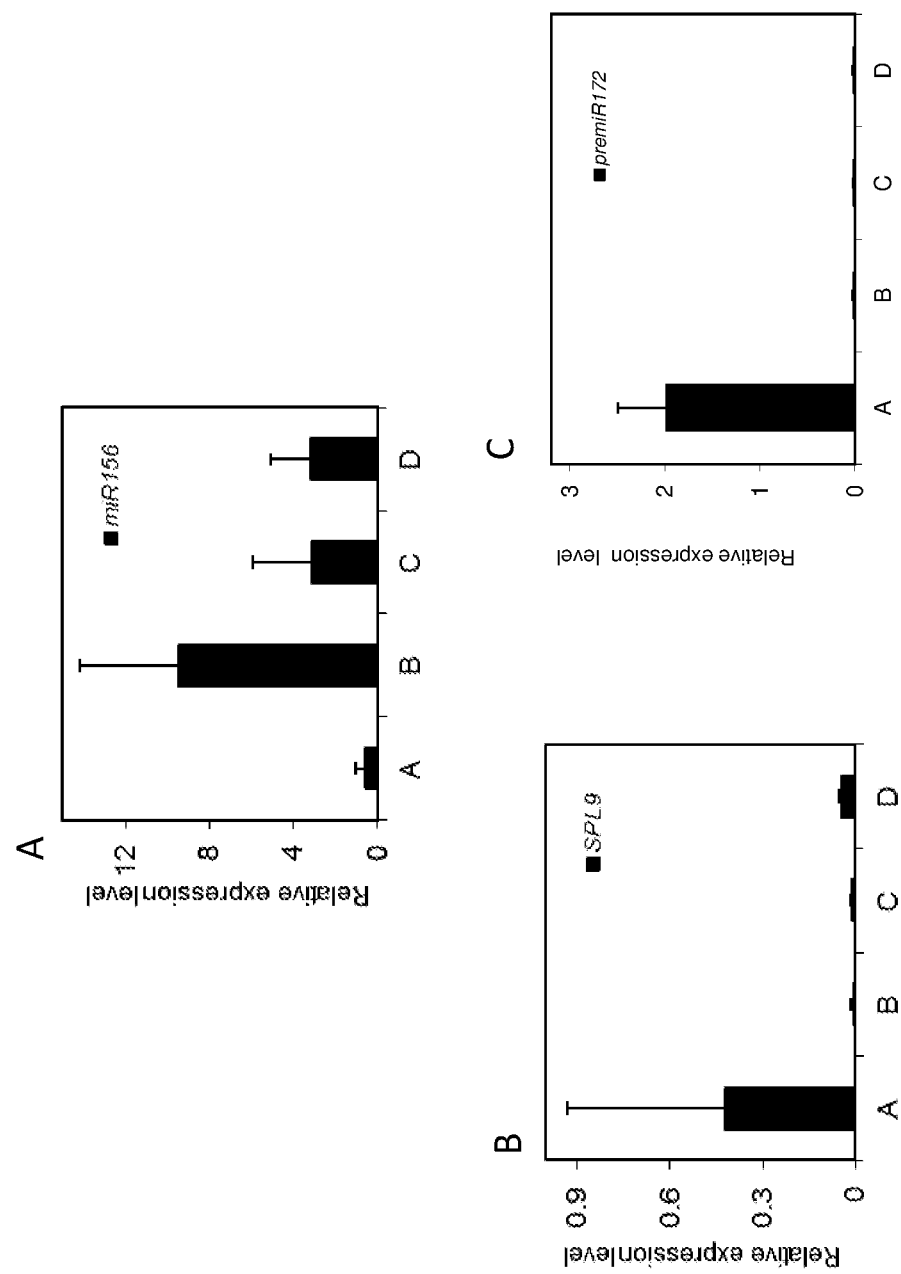
FIG. 11 shows the expression level of miR156 (A), SPL9 (B) and miR172 (C) in *Arabidopsis* seedlings. In particular, wild type plants grown for 48 h in a medium where wild type plants were grown for five days (column A); 35S::miR156 plants grown for 48 h in a medium where 35S::miR156 plants were grown for five days (column B); wild type plants grown for 48 h in a medium where 35S::miR156 plants were grown for five days (column C); and 35S::miR156 plants grown for 48 h in a medium where wild-type plants were grown for five days (column D).

The medium was analyzed for verifying the miR156 presence (FIG. 11A). The results indicated that the medium where the 35S::miR156 plants were grown is enriched in miR156 (sample B) when compared to the medium where the wild-type plants were grown for five days (sample A).

The medium sample C, which is the medium where the 35S::miR156 plants where grown for 5 days but then replaced with wild type plants, showed a decline in miR156 content (cfr. C with B). This result means that in the absence of 35S::miR156 plants, the miR156 content diminishes, or, alternatively, this means that the miR156 was taken-up by the wild type plants grown in C.

On the other hand, the miR156 content of sample D increased compared to sample A.

D is the medium where wild-type plants were grown for 5 days, and where 35S::miR156 plants were transferred for further 48 h.

The increase in miR156 content in this experimental condition is attributable to the release of miR156 in the medium (cfr. Medium A, which is a medium where wild-type plants were grown with medium D where wild-type plants were grown for 5-days but then 35S::miR156 plants were grown for 2 extra days).

The expression level of the miR156 target gene SPL9 was measured (FIG. 11B).

As expected, SLP9 gene expression was repressed when miR156 expression level was high, such as in 35S::miR156 plants and this was the case (Cfr. B with A).

Remarkably, the wild-type extract from plants that were transferred from two extra days in the medium conditioned by 35S::miR156 plants (sample C) displayed an SPL9 expression level that was comparable to that of 35S::miR156 plants (sample B) and not of wild type plants (sample A).

Therefore, miR156 molecules present in the conditioned medium were taken-up by wild-type plants in C, and this resulted in repression of the SPL9 gene.

As already said, SPL9 gene controls the expression of miR172. Therefore, in this experimental condition pre-miR172 expression should mirror that of SPL9. The results obtained confirmed this expectation (FIG. 11C)

In particular, the results demonstrate that miRNAs contained in a medium that was pre-conditioned by growing *Arabidopsis* seedlings overexpressing a specific miRNA are able to modulate the corresponding gene regulatory system. In the example provided the medium was enriched in miR156 by growing 35S:miR156 seedlings: as shown in FIG. 1 the level of miR156 is 10-times higher in "B" (where 35S:miR156 seedlings were grown) than in "A" (where wild-type seedlings were grown). Placing wild-type seedlings for 48 h in a medium enriched in miR156 (Sample "C") results in repression of the SPL9 gene and of the pre-miR172 gene, indicating that the miRNA molecules present in the medium were able to elicit gene silencing.

The invention claimed is:

1. A method, comprising:
   feeding a plant or seed a composition comprising a miRNA156 and/or miRNA399d containing extract, wherein the miRNA156 and/or miRNA399d containing extract is obtained from an exudate of a root of a non-transgenic plant and is used to improve the nutrient uptake, abiotic stress tolerance or growth in the plant or seed by interfering with gene expression through environmental RNA interference.

2. The method of claim 1, wherein the plant is a dicotyledonous or a monocotyledonous plant.

3. The method of claim 1, wherein the plant is selected from the group consisting of: Sugar beet (*Bela vulgaris*), Sugar cane (*Saccharum officinarum*), Corn (*Zea mays*) and Alfalfa (*Medicago saliva*).

4. The method of claim 1, wherein the composition further comprises micronutrients.

5. The method of claim 4, wherein the micronutrients are present in a concentration ranging from 0.1 to 20% w/w.

6. The method of claim 4, wherein the micronutrients are selected from the group consisting of KCl, $H_3BO_3$, $MnSO_4$, $CuSO_4$, $ZnSO_4$, and Fe-EDTA.

7. The method of claim 1, wherein the composition further comprises macronutrients.

8. The method of claim 7, wherein the macronutrients are present in a concentration ranging from 0.5 to 50% w/w.

9. The method of claim 7, wherein the macronutrients are selected from the group consisting of $KNO_3$, $Ca(NO_3)_2$, $MgSO_4$ and $KH_2PO_4$.

10. The method of claim 1, wherein the composition further comprises substances able to modify a surface tension, surfactants, adjuvants, adhesives, wetting compounds and substances able to facilitate transport of the composition inside the plant towards a target site.

11. The method of claim 1, wherein the composition is formulated as powder water soluble powder, granule, gel, tablet or emulsion, emulsifiable concentrate or as liquid solution or as liquid suspension.

12. The method of claim 1, wherein the feeding is by root feeding, leaf spraying, or any combination thereof.

13. The method of claim 1, further comprising applying biostimulants, hormones, plant growth regulators (PGRs), plant growth promoting Rhizobacteria (PGPR), or any combination thereof in combination with the feeding.

* * * * *